United States Patent
van de Zande

(10) Patent No.: US 7,601,500 B2
(45) Date of Patent: Oct. 13, 2009

(54) PRIME-BOOST VACCINE FOR THE PROTECTION OF EQUINES AGAINST VIRAL INFECTION

(75) Inventor: Saskia van de Zande, Geel (BE)

(73) Assignee: Intervet International B.V., Boxmeer (NL)

( * ) Notice: Subject to any disclaimer, the term of this patent is extended or adjusted under 35 U.S.C. 154(b) by 252 days.

(21) Appl. No.: 11/743,492

(22) Filed: May 2, 2007

(65) Prior Publication Data

US 2008/0014216 A1 Jan. 17, 2008

Related U.S. Application Data

(63) Continuation-in-part of application No. PCT/EP2006/067859, filed on Oct. 27, 2006.

(30) Foreign Application Priority Data

Nov. 1, 2005 (EP) ................................. 05110231

(51) Int. Cl.
*C12Q 1/68* (2006.01)
(52) U.S. Cl. ......................................................... 435/6
(58) Field of Classification Search ...................... 435/6
See application file for complete search history.

(56) References Cited

U.S. PATENT DOCUMENTS 4,693,893 A * 9/1987 Campbell ................. 424/206.1
6,177,082 B1 1/2001 Dowling et al.
6,436,408 B1 8/2002 Dowling et al.

FOREIGN PATENT DOCUMENTS

WO WO 2007/051763 A1 5/2007

OTHER PUBLICATIONS

European Medicines Agency: "European Public Assessment Report, Equilis Prequenza Te (Intervet International B. V.," Committee for Medicinal Products for Veterinary Use, Jul. 2005.

European Medicines Agency: "Equilis Prequenza Te; Summary of product characteristics" [Online] Jul. 2005, http://www.emea.eu.int/vetdocs/vets/Epar/equilisPrequenzaTe/equilisPrequenzaTeM.htm [retrieved on Mar. 9, 2006].

Minke, Jules Maarten et al., "Equine viral vaccines: the past, present and future," Veterinary Research, vol. 35, No. 4, Jul. 2004, pp. 425-443.

Chambers, T. M. et al., "A new modified live equine influenza virus vaccine: phenotypic stability, restricted spread and efficacy against heterologous virus challenge," Equine Veterinary Journal, vol. 33, No. 7, Nov. 2001, pp. 630-636.

Townsend, H. G. et al., "Efficacy of a cold-adapted, intranasal, equine influenza vaccine: challenge trials," Equine Veterinary Journal, vol. 33, No. 7, Nov. 2001, pp. 637-643.

Slater, J. et al., "Equine Immunity to Viruses," Veterinary Clinics of North America, Equine Practice, Saunders, Philadelphia, Pa., US, vol. 16, No. 1, Apr. 2000, pp. 49-68.

* cited by examiner

*Primary Examiner*—Ali R. Salimi
(74) *Attorney, Agent, or Firm*—William M. Blackstone

(57) ABSTRACT

It has been found that adequate protection against viral infection in equines can be achieved when vaccination with a live viral vaccine (prime) is followed by vaccination with an inactivated vaccine (boost) for the same virus, wherein the two shots are given no longer than 8 weeks apart.

The invention therefore provides a method for vaccination of equines against infection with an equine viral pathogen, wherein an animal is first vaccinated with a (prime) vaccine comprising an attenuated form of the pathogen, followed by a vaccination with a (boost) vaccine comprising the same pathogen in inactivated form, and wherein the boost vaccine is administered no longer than eight weeks after the prime vaccine.

The method of the invention is especially useful for vaccination against viral infections such as infections with EIV and/or EHV-1/EHV-4.

Especially for EIV, it has been found that when equines are vaccinated with such a prime-boost vaccine regimen according to the invention, the equines are protected against clinical signs after a challenge with a virulent EIV.

10 Claims, No Drawings

PRIME-BOOST VACCINE FOR THE PROTECTION OF EQUINES AGAINST VIRAL INFECTION

PRIORITY CLAIM TO RELATED PATENT APPLICATIONS

This application is a continuation in part of application PCT/EP2006/067859 filed Oct. 27, 2006.

The present invention is concerned with vaccinating equines against viral infection.

Equines are susceptible to a variety of infectious diseases. Due to the increasing international movement of horses the incidence of these diseases increases. Beside general sanitation, feeding, housing etc., vaccination of equines is therefore an important tool in preventing of animal suffering as well as the economic losses involved.

Infectious diseases for which horses can be vaccinated are, among others, equine influenza virus (EIV) and Equine herpes virus (EHV1 and EHV4) and Equine encephalitis (Western (WEE), eastern (EEE) and Venezuelan (VEE)) but also the West Nile virus, African horse Sickness, rabies, tetanus, Equine Infectious Anemia etc.

The vaccinations a given horse should receive depends on whether the horse is, for example, a domestic "backyard" horse, where insect borne diseases, such as EEE, WEE and VEE, or WNV may be a problem, or a horse which travels a lot and may be exposed to may other horses, where contagious viruses such as EIV may be a problem. Most horses are vaccinated against tetanus, since tetanus causes against a deadly disease in horses. In case the horse is, for example, a broodmare, the risk of abortion, for example associated with EHV infection, should of course be minimized. Moreover, some diseases may only be a problem in a particular part of the world, such as the Potomac horse virus or rabies.

Vaccines may be based on either a modified live (attenuated), an inactivated pathogen or on a subunit vaccine based on one or more important immunogens derived from a pathogen. Vaccines exist for each pathogen separate, but also combination vaccines, for example for protection against EIV, EHV and tetanus, exist.

Equine influenza is a major respiratory viral disease that causes flu like symptoms in equines. This disease is present throughout Europe, North America and parts of Asia. Disease symptoms caused by equine influenza virus can be severe, and are often followed by secondary bacterial infections which can lead to pneumonia and other problems. Horses of all ages are susceptible, but infection is most common in young unvaccinated horses. Most horses exposed to the virus will show signs within a period of 1-5 days and recover after 2-3 weeks.

Explosive outbreaks have been seen in susceptible populations. The virus can be spread easily from horse to horse as a result of droplets and also from nasal discharge and from things like infected brushes and rugs. The disease is very contagious and there is almost 100% infection rate in a population that has been previously unexposed to the virus. This often follows the import of infected horses from endemic areas not showing clinical signs, and is worsened by the fact that international transport of horses is increasing.

Equine influenza virus was discovered in horses around 1956 when it was recovered during an epidemic of respiratory disease among horses in Eastern Europe (Sovinová O. et al., Acta. Virol., 2, 51-61, 1958) The virus, A/Equine/Prague/1/56, (H7N7), is now designated as the prototype virus for equine influenza subtype-1. In 1963 another influenza virus, now designated subtype-2, was discovered during a major outbreak in the United States (Waddell G. H. et al., J. Am. Vet. Med. Assoc., 143, 587-590, 1963). For subtype-2, the prototype virus is A/Equine/Miami/1/63 (H3N8). The H3N8 subtype has meanwhile spread over the world and, at present, is the predominant virus subtype (The H7N7 subtype has not been isolated since 1980). The H3N8 subtype is prone to antigenic drift. Various variants of the H3N8 subtype co-circulate. Especially isolates circulating in Europe and the USA were antigenically distinguishable, the European lineage is represented by A/eq/newmarket1/93 (N/1/93) and the US lineage is represented by A/eq/Newmarket/2/93 (N/2/93) viruses (both Newmarket viruses were isolated from samples taken on the same day from vaccinated 2 year old Thoroughbred horses that has pyrexia and occasional coughing) (Daly et al., Vaccine 22, 4101-4109, 2004).

The prevention of equine influenza largely depends on vaccination. Vaccines based on the virus need to be updated regularly in order to reflect the most recent epidemiological situation. It has been recommended that vaccines for equine influenza contain a representative H3N8 from both the American and European lineages.

Reasonably effective vaccines, based on the two most important types of this virus, are available, but equines need to be vaccinated 2-3 times per year to ensure their immune status. However, the efficacy of inactivated (killed) virus vaccines is not always sufficient, and some times does not provide adequate protection for equines. Some inactivated vaccines can even produce undesirable side effects, for example, inflammatory reactions at the site of injection. Furthermore, inactivated vaccines are often not able to overcome maternal immunity in young foals, and can induce tolerance in a younger animal. Inactivated vaccines contain viral strains representing the "American type" equine influenza virus as well as the "European type" of the virus and need to be updated yearly with new strains as recommended each year by the WHO/OIE.

An attenuated live vaccine for equine influenza was developed by Heska. This vaccine Flu Avert IN was introduced by Heska in the United States in November 1999. Flu Avert I.N. vaccine is a "modified live" vaccine which incorporates a "cold adapted" virus that replicates only in the upper regions of the horse's respiratory system, but the virus does not replicate at the higher temperatures found in the lungs or lower respiratory tract of the animal. Heska's vaccine can be administered using a nasal applicator, rather than a needle. The cold-adapted virus strains were developed at the University of Pittsburgh by Drs. Patricia W. Dowling and Julius S. Youngner (U.S. Pat. No. 6,177,082 B1).

Equine herpes virus 1 (EHV-1) and equine herpes virus 4 (EHV-4) are an important cause of respiratory disease and abortion in horses world-wide. Especially when inactivated vaccines against EHV are used, the vaccine should contain a representative of both subtypes in order to provide adequate protection.

Such vaccines are commercially available, either alone, or in combination with, for example, influenza and tetanus, such as Equilis Resequin (Intervet International BV), which contains inactivated EHV-1 strain racH, inactivated EHV-4 strain 2252, and three inactivated EIV strains (representatives of the European and American type EIV).

A modified live vaccine for vaccination of equines against EHV infection, based on the attenuated EHV-1 strain racH, exist as well (Prevaccinol, Intervet International BV.

It has now been found that adequate protection against viral infection in equines can be achieved when vaccination with a live viral vaccine (prime) is followed by vaccination with an inactivated vaccine (boost) for the same virus, wherein the two shots are given no longer than 8 weeks apart.

The invention therefore provides a method for vaccination of equines against infection with an equine viral pathogen, wherein an animal is first vaccinated with a (prime) vaccine comprising an attenuated form of the pathogen, followed by a vaccination with a (boost) vaccine comprising the same pathogen in inactivated form, and wherein the boost vaccine is administered no longer than 8 weeks after the prime vaccine.

The invention further relates to the use of an inactivated equine viral pathogen, to prepare a boost vaccine for vaccinating equines that have been vaccinated with a priming vaccine, containing the same pathogen in an attenuated live form, no longer than 8 weeks prior to being vaccinated with the boost vaccine.

Preferably the two shots are given no longer than 6 weeks apart, for example, between 3-6 weeks apart, preferably between 4-6 weeks apart.

With "equine viral pathogen" is meant a virus that causes an infectious disease in equines. The method of the invention is especially useful for vaccination against viral infections such as infections with EIV and/or EHV-1/EHV-4.

For EIV, it has been found that when equines are vaccinated with such a prime-boost vaccine regimen according to the invention, the equines are protected against clinical signs after a challenge with a virulent EIV.

Moreover, the equines are completely protected against viral shedding and no virus could be isolated from any vaccinated equines at any time. The prime boost vaccination according to the invention provides sterile immunity, which hitherto, could not be demonstrated for any vaccine against equine influenza. Even when the animals were challenged with a very recent strain of influenza, the prime boost vaccination according to the invention provided sterile immunity against challenge with this recent virus.

The prime vaccine used in the present invention contains the viral pathogen in attenuated live form, meaning that the viral pathogen has been modified in such a way that it does not cause the disease, but still elicits an immune response in the vaccinated animal that attributes to protection against infection with the pathogen.

In case of EIV the prime vaccine comprises an attenuated live equine influenza virus. The attenuated live virus may, for example, be a temperature sensitive mutant of the equine influenza virus. If the vaccine is based on a temperature sensitive mutant of the equine influenza virus, for example a ts mutant which only replicated at the (lower) temperatures in the upper respiratory tract, the vaccine is preferably administered via the intranasal route. Cold-adapted equine influenza viruses and vaccines based thereon are, for example, disclosed in U.S. Pat. No. 6,436,408. An example of a vaccine that can be used as the prime vaccine in the prime-boost regimen according to the invention is the commercially available modified live vaccine Flu Avert I.N. (Heska Corp).

In case of a prime vaccine for EHV1/EHV-4 infection, the vaccine contains an attenuated EHV strain. An preferred example of an attenuated live EHV-1 strain that can be used in a prime vaccine as used with the method of the invention is the racH strain. This strain has served as the basis for modified live vaccines against EHV infection such as Prevaccinol (Intervet International BV). Such a vaccine can be used as the prime vaccine in the present invention. In a preferred embodiment of the invention the prime vaccine further contains an adjuvant.

The prime vaccine further contains the normal constituents of a modified live vaccine, such as a suitable pharmaceutical carrier which is usually a buffered diluent, optionally a preservative, etc., or any other suitable constituent known to the skilled person. The modified live vaccine may be administered via any suitable administration route.

The boost vaccine used with the invention contains the equine viral pathogen in an inactivated form.

In case the prime boost vaccination according to the invention is used to protect equines against infection with EIV, the boost vaccine comprises an inactivated equine influenza virus. Vaccines based on inactivated influenza are known in the art. An inactivated vaccine may contain the virus as whole virus (inactivated viral particles) or as subunits (a vaccine containing heamagglutinin and neuraminidase subunits of the virus) in a suitable amount. Suitable amounts of the inactivated virus are known in the art. Good results were obtained when the boost vaccine was the "Equilis Prequenza" vaccine (developed by Intervet International BV), which is adjuvated with an Iscom matrix based adjuvant.

A boost vaccine for use in a prime boost vaccination according to the invention, for the protection against EHV-1, may contain inactivated strains of both EHV-1 and EHV-4. Such inactivated vaccines against EHV are known in the art.

At least the boost vaccine used with the invention may contain at least two inactivated viral pathogens. For example, a combination vaccine may be used that contains both inactivated strains of EIV, as well as inactivated strains of EHV. Optionally the boost vaccine may contain further immunogens derived from other pathogens such as, for example, tetanus.

Inactivated combination vaccines against EIV/EHV & tetanus are known in the art (for example, Equilis Resequin and Equilis Resequin Plus (Intervet International BV).

The prime boost vaccination according to the invention can be applied to more than one pathogen at the same time.

For example, the prime vaccination for both pathogens may be given in the form of separate priming vaccinations, one for each pathogen, or in the form of a one-shot priming vaccination where attenuated live forms of different pathogens are combined in a combined live vaccine. For example, attenuated live strains of EIV and EHV may be combined in one and the same vaccine formulation, or may be give separately in two separate formulations, both used as priming vaccine in a method of the invention. The boost vaccination may then also be given in separate or combined form.

Either the boost or the prime vaccine may be combined in one and the same formulation with other immunogens such as, for example, purified tetanus toxoid, also when these other pathogens are not administered in a prime boost vaccine regimen according to the invention. Thus, for example, purified tetanus toxoid may be part of the boost vaccine. Thus, existing inactivated combination vaccines can be used as the boost vaccine in the present invention, when combined with a priming vaccination for one of the viral pathogens, which priming vaccination contains the pathogen in attenuated live form.

An inactivated boost vaccine as used in the invention may contain a suitable adjuvant. Suitable adjuvants are known in the art. For example, a suitable adjuvant may be based on Quillaja bark extracts or one or more saponin fractions thereof. Saponin fractions are produced from Quillaja bark extracts (Quil A) (Morein et al., Clin. Immunother., 3(6), 461-475, 1995: "Immunostimulating Complexes, clinical potential in Vaccine Development"). Saponin fractions may be used as such, or in the form of a immunestimulatory complex such a s an ISCOM or ISCOM matrix, based on the saponins, a sterol and a lipid. Examples of suitable saponins fractions, and ISCOMs and matrices based thereon are given in Morein et al. (supra) and in WO96/11711. Useful fractions are for example "fraction A" or "Fraction C" of Quil A or mixtures thereof. The "Equilis Prequenza" vaccine as developed by (Intervet International BV), is adjuvated with an Iscom matrix based adjuvant. Equilis Equenza (Intervet International BV) is adjuvated with Quil A.

Preferably both the prime(live) and boost vaccines are adjuvated with a saponins based adjuvant.

In a preferred vaccine combination according to the invention a vaccine containing live EHV strain racH, is used for the "prime" vaccination, in combination with a "boost" vaccine, said boost vaccine comprising inactivated EHV1/EHV4 virus, optionally combined with inactivated EIV strains (recommended EIV strains). Both the prime and the boost vaccine are advantageously adjuvated with an adjuvant based on Iscom matrices based on purified saponin fractions, such as "fraction A" or "Fraction C" of Quil A or mixtures thereof, as mentioned above.

EXAMPLES

Example 1

Comparison of Different Vaccination Schedules

The purpose of this study was to compare different vaccination schedules, using the modified live vaccine Flu avert IN against a challenge with A/equine/2/South-Africa/04/03 considering the recommendation of the OIE to update new influenza vaccines with the South-African strain.

Twenty-four Fjord yearlings were obtained and housed on a pasture.

Seven horses were vaccinated twice with one dose of Flu Avert IN at four weeks interval (group A).

Seven horses were vaccinated with one dose of Flu Avert IN and four weeks later with one dose of Equilis Prequenza Te (group B).

Six horses were vaccinated ones with one dose of Flu Avert IN to determine the onset of immunity (group C).

Four animals were left unvaccinated to serve as control (group D).

Flu Avert IN contains the equine influenza virus strain P821 which is a cold adapted, temperature sensitive mutant of equine influenza type A2 derived from parent virus A/equine/2/Kentucky/1/91. The vaccine was registered by Heska Corporation and is distributed in the USA by Intervet inc.

Euqilis Prequenza Te is a suspension for injection containing:

| Active substances: Purified haemagglutinin subunits from equine influenza viruses: | |
|---|---|
| A/equine-1/Prague/1/56 | 100 AU (antigenic units) |
| A/equine-2/Newmarket/1/93 | 50 AU |
| A/equine-2/Newmarket/2/93 | 50 AU |
| Adjuvant: | |
| Purified saponins | 375 ug (microgram) |
| Cholesterol | 125 ug |
| Phosphatidylcholine | 62.5 ug |
| Excipient | |
| Thiomersal traces | |

The vaccine was registered by Intervet International BV.

Three weeks after the second vaccination (groups A and B) or one week after the vaccination (group C) all horses were challenged by aerosol with A/equine-2/South Africa/04/03 virus. After challenge horses were monitored for clinical signs of influenza, body temperature, virus excretion and serology. Blood samples were taken during course of the vaccination and challenge to determine the antibody levels (HI test) against different vaccine strains.

At moment of challenge the horses in group A had a mean HI titre of 6.0 and 5.7 against Newmarket/1/93 and Newmarket/2/93 respectively, the horses in group B had a mean HI titre of 6.1, 11.1 and 10.3 against Prague/1/56, Newmarket/1/93 and Newmarket/2/93 respectively. The horses in group C had no HI antibodies at moment of challenge. After challenge all the horses responded well against the Newmarket/1/93 strain, mean HI titres in group A, B, C and D at two weeks after challenge were: 10.9, 10.3, 10.3 and 9.5 respectively.

After challenge the non-vaccinated animals and the horses of group C showed characteristic signs of influenza such as a marked mucopurulent discharge and fever. The vaccinated animals in group A and B showed only mild signs. Virus was isolated from a few horses in group A and from none of the horses of group B. Virus was isolated from all the horses of group C between at 3 days post challenge (dpc) while all the horses of group D shed virus from day 1 till 6 dpc. All parameters examined in the statistical analysis such as the temperature score, the total clinical scores and the duration of virus excretion were significantly lower in the vaccinated animals of group A and B compared to the non-vaccinated group.

It is concluded that the prime boost vaccination course, Flu Avert IN followed by Equilis Prequenza 4 weeks later, strongly reduces clinical signs and induces a sterile immunity when challenged with the recent isolated equine influenza virus strain SA/04/03. Two times Flu Avert with 4 week interval gave also a good protection against SA/04/03 comparable with the protection archived by the recommended basic vaccination course of Equilis Prequenza. Furthermore, the onset of immunity of Flu Avert IN is very rapid, naive horses were partially protected against SA/04/03 challenge 7 days after the vaccination. It is interesting to investigate the onset of immunity of Flu Avert in previously primed animals.

Example 2

Challenge With Recent Influenza Strain After Prime Boost Vaccination

In a previous study, reflected in Example 1, it was demonstrated that horses showed a sterile immunity when they were primed with the live Flu Avert IN vaccine and boostered 4 weeks later with Prequenza. The purpose of this study was to reconfirm this observation using another challenge virus.

Eight Fjord yearlings were obtained and housed on a pasture. Four horses were vaccinated with one dose of Flu Avert IN and four weeks later with one dose of Equilis Prequenza Te (group A) and four animals were left unvaccinated to serve as control (group B). Three weeks after the second vaccination all horses were challenged by aerosol with A/equine-2/Newmarket/05/03 virus. After challenge horses were monitored for clinical signs of influenza, body temperature, virus excretion and serology. Blood samples were taken during course of the vaccination and challenge to determine the antibody levels (HI test) against different vaccine strains.

At moment of challenge the horses in group A had a mean HI titre of 6.0 and 5.7 against Newmarket/1/93 and Newmarket/2/93 respectively. After challenge all the horses responded well against the Newmarket/1/93 strain, mean HI titres in group A and B at two weeks after challenge were:

10.9 and 9.5 respectively. After challenge the non-vaccinated animals showed characteristic signs of influenza such as a marked mucopurulent discharge, coughing and fever. The vaccinated animals showed only mild signs. No virus was isolated from the vaccinated horses. Virus was isolated from all the control horses between 2 and 6 days post challenge (dpc). All parameters examined in the statistical analysis such as the temperature score, the total clinical scores and the duration of virus excretion were significantly lower in the vaccinated animals compared to the non-vaccinated group.

It is concluded that the prime boost vaccination course, Flu Avert IN followed by Equilis Prequenza 4 weeks later, strongly reduces clinical signs and induces a sterile immunity when challenged with the recent isolated equine influenza virus strain Newmarket/05/03. In general it is clear that when horses that are primed with Flu Avert IN and receive a booster 4 weeks later with Prequenza, a sterile immunity against equine influenza can be archived after challenge.

Example 3

Different (EIV/)EHV Vaccination Protocols Against a Challenge With EHV-1

Twenty-five horses (with a low VN titre against EHV-1 and 4) were divided in 5 groups of 5 horses each.

Each horse was vaccinated IN or IM according to Table 1. One dose IM (1 or 2 ml) will be applied with a 2 ml syringe with green needle (0.8×40 nm).

At t=0 weeks horses in group A and D were vaccinated intranasally (IN) with attenuated live herpesvirus strain Rac H live vaccine (A and D). The horses in group C and D were vaccinated intramuscularly with Rac H inac vaccine containing a high antigenic mass, or with an inactivated EIV/EHV combination vaccine.

At T=4 weeks horses in groups C, D and E received a booster vaccination intramuscularly with an inactivated EIV/EHV combination vaccine (D and E) or Rac H inac with high antigenic mass vaccine (C). Group F served as control group.

Body temperatures were measured and nasopharyngeal swabs were taken at day of vaccination. Blood samples for serology were taken at the time of vaccination, 7, 28 and 49 days after the first vaccination. Heparin blood samples were taken at each time of vaccination.

At 3 weeks after the second vaccination all horses were challenged intranasally with EHV-1 strain M8. Starting 1 day before challenge, the horses will be observed daily for a period of 15 days for any clinical signs of herpesvirus. For the same period of time body temperatures will be measured and nasopharyngeal swabs will be taken daily for a period of 14 days after challenge. Blood samples for serology were taken at the time of challenge, and will be taken 7 and 14 days after challenge. Heparin blood samples were taken at time of challenge and will be every two days during 14 days.

Materials and Methods

Vaccine Formulations:

| Formulation 1: | Live EHV vaccine (prevaccinol) | |
| Pharmaceutical form: | Liquid | |
| Composition: | Live EHV-1 (Rac H), $6.0 \log_{10} TCID_{50}$/ml vaccine | |
| | Adjuvant purified saponins | 250 µg/ml vaccine |
| Formulation 2: | Rac H inac High AM | |
| Pharmaceutical form: | Liquid | |
| Composition: | EHV-1 (Rac H) | 10000 AU/ml vaccine |
| | Adjuvant: purified saponins | 250 µg/ml vaccine |
| Formulation 3: | inac EIV/EHV combination vaccine | |
| Pharmaceutical form: | Liquid | |
| Composition: | South Africa/03 | 450 AU/ml vaccine |
| | Newmarket/02 | 450 AU/ml vaccine |
| | EHV-1 (Rac H) | 1000 AU/ml vaccine |
| | EHV-4 (2252) | 5000 AU/ml vaccine |
| | Tetanus toxoid | 40 LF/ml vaccine |
| | Adjuvant purified saponins | 250 µg/ml vaccine |
| Challenge: | EHV-1 M8: | |
| Volume: | approximately 4 ml per animal | |
| Dosage: | $10^{7.5}$ EID$_{50}$ per animal | |
| Route: | 1 ml intranasal | |

TABLE 1

Vaccination schedule

| Group (no. of horses) | 1$^{st}$ vaccination (t = 0) Vaccine volume/route | 2$^{nd}$ vaccination (t = 4 weeks) Vaccine volume/route | Challenge (t = 7 weeks) |
|---|---|---|---|
| A (5) | Rac H live 1 ml IN | — | EHV-1 M8 |
| C (5) | Rac H inac 1 ml IM | Rac H inac 1 ml IM | EHV-1 M8 |
| D (5) | Rac H live 1 ml IN | Inac EIV/EHV combi Resequin 2 ml IM | EHV-1 M8 |
| E (5) | Inac EIV/EHV combi 2 ml IM | Inac EIV/EHV combi 2 ml IM | EHV-1 M8 |
| F (5) | — | — | EHV-1 M8 |

Interpretation of Results

Clinical observations, rectal temperatures and virus re-isolation data give an indication of the efficacy induced by the different EHV-1 vaccines against the EHV-1 challenge virus. Serology data, heparin blood samples and the nasal swabs taken at first and second vaccination and time of challenge confirm the negativity of the animals at the start of the challenge.

The invention claimed is:

1. A method for vaccination of an equine animal against infection with an equine viral pathogen, comprising vaccinating the animal with a primer vaccine comprising an attenuated form of the pathogen, followed by vaccinating with a booster vaccine comprising the same pathogen in inactivated form, wherein the booster vaccine is administered no longer than eight weeks after the primer vaccine, and wherein the pathogen is equine herpes virus (EHV).

2. The method according to claim 1, wherein at least the booster vaccine contains at least two inactivated viral pathogens.

3. The method according to claim 2, wherein the booster vaccine comprises inactivated EIV and inactivated EHV.

4. The method according to claim 1, wherein the primer vaccine comprises live attenuated EHV.

5. The method according to claim 1, wherein the primer vaccine further comprises an adjuvant.

6. The method according to claim 1, wherein the booster vaccine further comprises an adjuvant.

7. The method according to claim 1, wherein the adjuvant is based on an ISCOM matrix.

8. The method according to claim 6, wherein the adjuvant is based on an ISCOM matrix.

9. The method according to claim 1, wherein the animal is vaccinated more than once with a primer vaccine.

10. The method according to claim 1, wherein the primer vaccine comprises at least two viral pathogens.

* * * * *